United States Patent [19]

Wieder

[11] 4,058,732
[45] Nov. 15, 1977

[54] METHOD AND APPARATUS FOR IMPROVED ANALYTICAL FLUORESCENT SPECTROSCOPY

[75] Inventor: Irwin Wieder, Los Altos, Calif.

[73] Assignee: Analytical Radiation Corporation, Los Altos, Calif.

[21] Appl. No.: 591,305

[22] Filed: June 30, 1975

[51] Int. Cl.$^2$ ............................................. G01N 21/38
[52] U.S. Cl. .................................................. 250/461 B
[58] Field of Search .................... 250/461 B, 301, 269; 424/7

[56] References Cited

U.S. PATENT DOCUMENTS

| 3,842,264 | 10/1974 | Arnold et al. | 250/269 X |
| 3,886,363 | 5/1975 | Ohnishi et al. | 250/461 B X |
| 4,006,360 | 2/1977 | Mueller | 250/461 B |

OTHER PUBLICATIONS

"Gated Nanosecond Time Resolved Emission Spectroscopy Separation of Mixed Emissions from Carbonyl Compounds", R. E. Brown et al., *Analytical Chemistry*, vol. 46, p. 1690 (1974).

Primary Examiner—Davis L. Willis
Attorney, Agent, or Firm—Thomas Schneck, Jr.

[57] ABSTRACT

A method is disclosed whereby the molecules of a chemical substance to be measured, referred to as target molecules, are combined with fluorescent molecules having a relatively long fluorescent decay lifetime. These tagged target molecules are excited with an intense pulse of ultraviolet or visible radiation, and a detection system is gated on only after background fluorescence has substantially decayed, but while the fluorescent tag attached to the target molecules is still actively decaying. The amount of fluorescent tag emission which is measured is indicative of the target molecule content of the sample. An apparatus for improved fluorescent spectrofluorometry includes a pulsed excitation source and a gating means connected to a detection system for gating the detection system on after tagged target molecules have been excited and competing background fluorescence has substantially decayed, but before tagged target molecules have substantially decayed.

25 Claims, 4 Drawing Figures

— TYPICAL EXCITATION PULSE WITH DURATION OF 3 NANOSECONDS.

— TYPICAL BACKGROUND FLUORESCENCE DECAY WITH LIFETIME OF 10 NANOSECONDS.

GATE ON

— TYPICAL FLUOROTAG FLUORESCENCE DECAY WITH LIFETIME OF 100 NANOSECONDS.

GATE OFF

TIME (NANOSECONDS)

METHOD AND APPARATUS FOR IMPROVED ANALYTICAL FLUORESCENT SPECTROSCOPY

BACKGROUND OF THE INVENTION a. Field of the Invention

The invention relates to spectrofluorometers, and more particularly to an improved spectrofluorometric method and apparatus which minimizes the effect of background or competing fluorescence.

b. Prior Art

In fluorescent spectroscopy, a sample containing a material of unknown quantity, i.e. target molecules, is placed in a holder. The sample may be in the form of a liquid solution or a solid on a substrate such as filter paper. The sample is then exposed to radiation of known spectral distribution, characteristically a restricted bandwidth of light. The distribution of excitation radiation is within the excitation spectrum of target molecules and preferably near the maximum. The emission spectrum following irradiation is at longer wavelengths and is characteristic of the target molecules. Its intensity is measured to indicate the quantity of target molecules.

One problem with present spectrofluorometers is that their sensitivity is limited due to noise in the excitation and detection systems and secondly, due to competing fluorescence from ambient substances, such as from substrate materials, sample containers, particles in the air, other fluorescing species in the sample, reagents and the like.

Prior to the filing of this patent application, a pulsed dye laser has been reported for use in a spectrofluorometer. See the article entitled "New Type of Spectrofluorometer with a Tunable Laser Source and Unique Optical System" by D. C. Harrington and H. V. Malmstadt, *Analytical Chemistry*, Vol. 47, No. 2, February 1975, p. 271-276.

Use of a pulsed laser to stimulate fluorescent emission from target molecules improves the signal to noise ratio to a certain extent. However, while the signal to noise ratio is enhanced, the problem of competing fluorescence is still present. When the amount of target material is very small, perhaps a few parts per billion or less, the fluorescence of the target molecules may not be detected because it may be weaker than the combined fluorescence from all background sources.

It is therefore an object of the invention to provide a method for detecting very small quantities of target molecules in the presence of competing background fluorescence.

Another object is to devise an improved spectrofluorometer for detecting very small quantities of target molecules in the presence of competing background fluorescence.

SUMMARY OF THE INVENTION

I have devised a new method for fluorescent spectroscopy of target substances which includes the steps of first isolating molecules of target substances and then tagging target molecules with a fluorescent tag having a relatively long fluorescent decay lifetime compared with the decay lifetime of ambient substances. These ambient substances may have emission spectra in the same wavelength range as target molecules. Next, the tagged target molecules are excited with intense pulses of radiation having the appropriate spectral distribution, i.e. within the excitation spectrum of target molecules and preferably near the maximum, each pulse having a pulse duration which is short compared with the relatively long fluorescent decay lifetime of the fluorescent tag. Then, a fluorescence detection system is gated on only after the fluorescence of ambient substances, which cause the deleterious competing fluorescence, has substantially decayed.

A new fluorescent spectrofluorometer is utilized, providing an intense pulsed excitation source for target molecules by means of a pulsed excitation source, such as a pulsed dye laser excited by a nitrogen laser or by a nitrogen laser alone. A fluorescent detection system, i.e. a detection means, typically utilizing a photomultiplier, is spaced apart from the excitation source and positioned to receive fluorescent radiation emission from target molecules and ambient substances in response to excitation pulses. An electronic gate turns the detection system on only after competing fluorescence has decayed.

Utilizing the method and apparatus disclosed herein, competing fluorescence has substantially decayed at the time the detection system is gated on, so that the detection system can measure the emission spectra of the target molecules only.

DESCRIPTION OF THE PREFERRED EMBODIMENT

Figure 1:
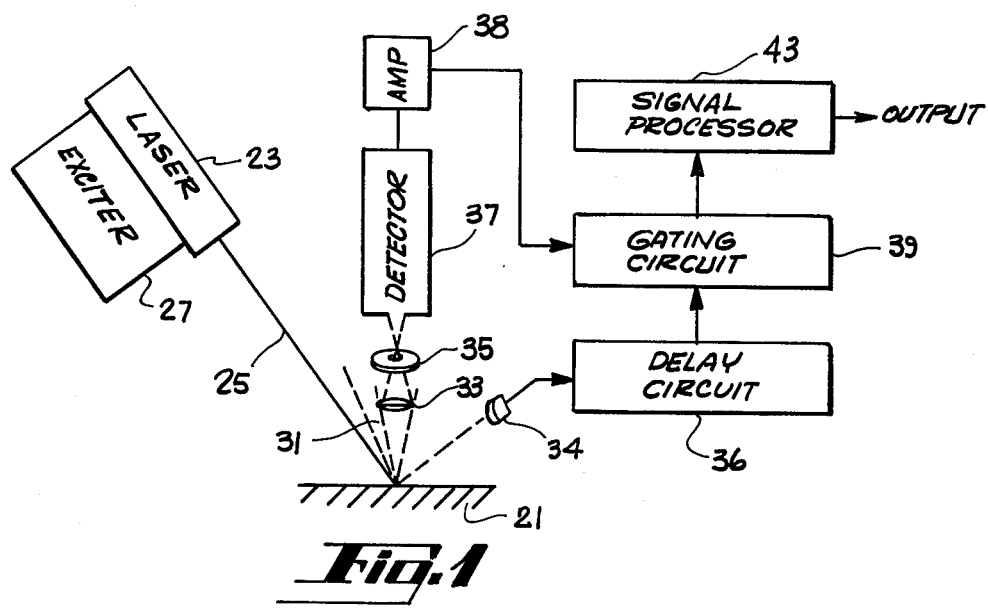
FIG. 1 is a plan view of the apparatus of the present invention.

In the method of the present invention, it is necessary to tag target substances, the quantity of which is to be determined, with a fluorescent tag which has a relatively long fluorescent decay lifetime, compared with decay lifetimes of ambient substances. The target material has been previously separated from other substances by known techniques, such as by chromatography or by antibody fixation.

An example of separation by antibody fixation is as follows. A quantity of antibody specific to a target material is deposited on a solid matrix, such as cellulose acetate. An unknown quantity of target molecules in solution and specific to the selected antibodies is exposed to the matrix and reacts with the selected antibodies thus becoming fixed to the substrate. See the article entitled, "The Fluorescent Antibody Technique Applied to Titration and Identification of Antigens in Solutions or Antisera" in *Proc. Soc. Experimental Biology*, Vol. 113, p. 394-397 by F. Paronetto (1963), which is incorporated by reference herein.

Once a separation of the target material is achieved a fluorotag, i.e. a fluorescent tagging material having an affinity for the target material, is used to tag the target and the excess tag is washed away.

At least two types of fluorescent tags may be utilized. Each fluorotag is selected to have a period of fluorescence long compared to competing background fluorescence. For example, a fluorotag whose decay lifetime is at least ten times the duration of competing background fluorescence would be desirable. Either of the exemplary fluorotags discussed below may be used with each of the separation methods.

A first exemplary class of fluorotags consists of rare earth-organo complexes. These consist of a rare earth bound to an organic compound with the resulting complex having desired properties. These properties are efficient excitation at convenient wavelengths, good excitation transfer to the rare earth, high quantum efficiency at ordinary temperatures, narrow emission spectrum, and very long lifetimes. It is believed that the complex transfers its excitation to the rare earth and it is the intensity of the emission spectra of the rare earth which is measured and correlated with the amount of rare earth-organo complex present. If rare earth-organo complex molecules have been bound to a target molecule in a fixed ratio, the amount of target material can be inferred in accord with the method and apparatus disclosed herein.

Representative rare earth-organo complexes which have been found to have the above desired properties are europium benzoylacetonate and europium benzoyltrifluoroacetonate. The fluorescence of the former compound and other similar compounds is discussed by S. I. Weissman in the *Journal of Chemical Physics*, Vol. 10, p. 214–217, 1942, incorporated by reference herein.

Another class of fluorotags which have relatively long decay lifetimes, over 100 n.s., is represented by pyrenebuterate. Preparation of pyrenebuterate and typical fluorescent lifetimes are discussed by Knopp and Weber in the *Journal of Biological Chemistry*, Vol. 242, p. 1353 (1967) and Vol. 244, p. 6309 (1969), incorporated by reference herein.

The fluorotags may be attached to target molecules, depending on the target, in two ways: by ordinary chemical combination (non-specific), or by biological chemical action (specific). In the latter case, fluorescent antibodies, specific to the target antigens, are selected for capture by the antigens in a known ratio and the excess fluorotag is washed away. The procedure for tagging antigens with fluorescent antibodies is described in *Fluorescent Antibody Techniques and Their Applications*, A. Kawamura, Ed., University Park Press, Baltimore, MD., 1969, incorporated by reference herein.

The preparation of an antibody conjugate with pyrenebutyrate, i.e. a fluorescent antibody, is described in the article "The Rotational Diffusion of Thyroglobulin" in the *Journal of Biological Chemistry*, Vol. 244, No. 23, 1969, p. 6543–6547 by A. W. Rawitch et al., incorporated by reference herein.

Referring now to FIG. 1, the target molecules have been isolated on a substrate, tagged and supported, as by support 21. The tagged target substance is excited by excitation source 23, having a known output spectrum. Usually the output is in the form of a beam 25 which is substantially monochromatic, and in the present embodiment, pulsed radiation, typically from a laser is employed. The pulse duration is at least ten times shorter than fluorotag fluorescence lifetime. We have found that a tunable dye laser excited by a pulsed nitrogen laser exciter 27 causes a very strong excitation. Alternatively a pulsed nitrogen laser alone operating at 3371A causes very strong excitation. Either laser is preferred because high peak power and relatively short duration pulses can be obtained, at a wavelength within the excitation spectrum of most substances.

Alternatively, the filtered and focused output from a simple pulsed gas discharge can also be used, provided its duration is at least ten times shorter than the fluorescent lifetime of the fluorotag.

Beam 25 is directed toward target molecules on support 21. The target molecules may alternatively be in solution in a vial.

Emission from substrate 21 is indicated by the dashed lines 31 which are collected by a lens 33 and passed through a filter, such as an interference filter 35 and thence to a detector 37, which is typically a photomultiplier tube. Interference filter 35 has a wavelength bandpass centered at the emission wavelength of the emission radiation of the fluorescent tagging material and filters out excitation wavelength radiation from source 23 scattered toward detector 37.

Detection 37 which is "on" at all times produces an electrical signal proportional to the fluorescent radiation emission received and which is amplified by a linear amplifier 38 which then passes the amplified signals to a gating circuit 39. The gating circuit is opened (on) and closed (off) by two signals from delay circuit 36. These two signals are generated at two fixed times after the excitation pulse is sensed by phototube 34. The resulting signal from phototube 34 starts a timing sequence in circuit 36 which then generates the delayed signals.

The amount of delay selected in the delay circuit 36 for the first signal is preferably selected to be at least 5 background fluorescent lifetimes. For example, if the lifetime of background or ambient fluorescence is 10 nanoseconds, the selected first delay is preferably 50 nanoseconds. If the decay of ambient fluorescence is by an exponential decay mode, 5 decay lifetimes represent a reduction in the background or ambient fluorescence to about 0.7% of its peak value.

Gating circuit 39 is kept open until the second delayed signal from delay circuit 36 arrives. This should be at a time preferably 2 decay lifetimes of the fluorescent tag, for example, approximately 200 nanoseconds for pyrenebutyrate.

After signal gating by the gating circuit 39 which acts as a switch, the linearly amplified signal from amplifier 38 passes into the signal processor 43 which averages the results of many pulses and which correlates the amplified signal with information characterizing the emission of known quantities of the target material. The output of signal processor 43 is thereby indicative of the quantity of target molecules.

Figure 2A:
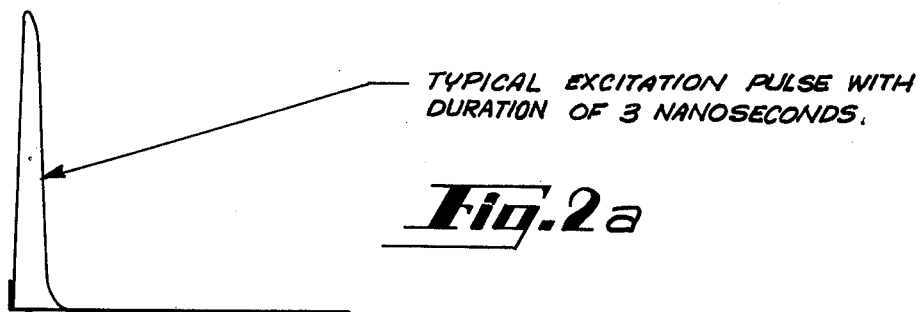
FIG. 2a is an intensity plot versus time of a laser excitation pulse.

In FIG. 2a, the pulse amplitude of an excitation pulse is shown by the ordinate axis and time is shown as the abscissa. The duration of the pulse (time between its half-intensity points) is indicated by the arrow and is shown to be 3 nanoseconds. When fluorescent lifetime (not duration) is discussed herein, lifetime is defined as the time at which the fluorescent intensity has decayed to $1/e$ of its initial value where $e$ is the base of the natural system of logarithms.

Figure 2B:
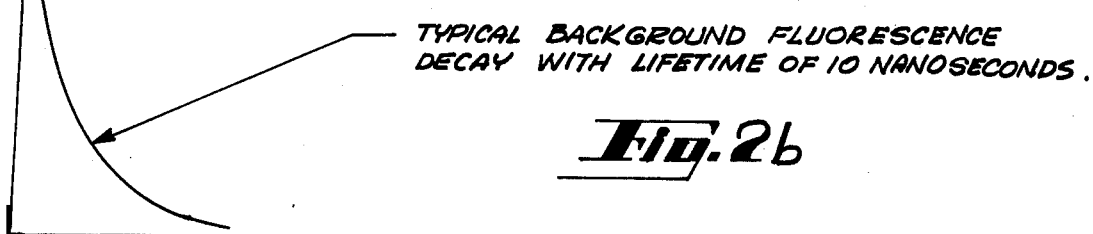
FIG. 2b is an intensity plot versus time of fluorescent emission of ambient substances.

FIG. 2b illustrates ambient fluorescence relative to an excitation pulse with the same zero starting time as in FIG. 2a. The intensity of ambient fluorescent is shown as the ordinate and time as the abscissa in plot. The lifetime of ambient fluorescence, i.e. combined from all sources, including particles in the air, reagants, holder materials, other fluorescing species in the sample and the like is shown to be approximately 10 nanoseconds and decays toward zero.

Figure 2C:
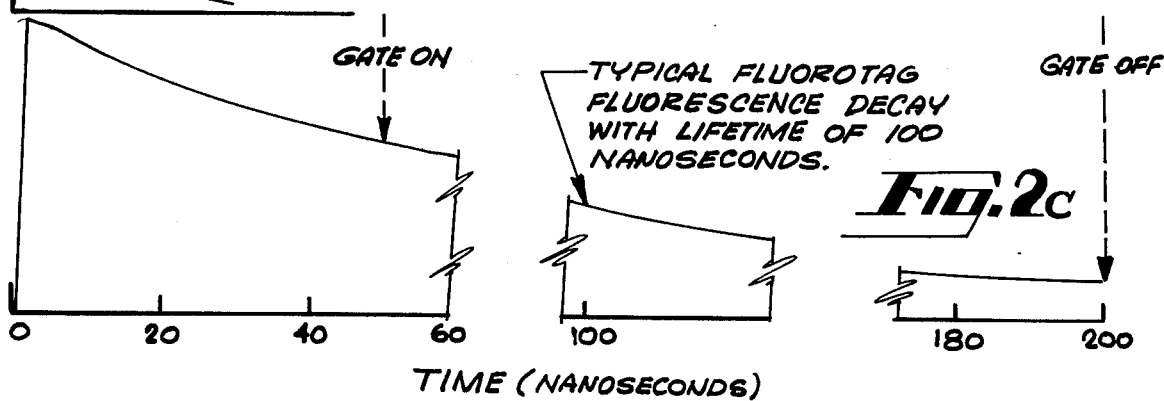
FIG. 2c is an intensity plot versus time of the emission of tagged target molecules in accord with the method of the present invention.

In FIG. 2c, the intensity of a typical fluorescent tag material is plotted, with the intensity shown as the ordinate and time shown as the abscissa. The lifetime is shown to be 100 nanoseconds, as indicated by the arrow in FIG. 2c. FIG. 2c shares a common zero time with FIGS. 2a and 2b and the time gating circuit is held off is indicated to the left of the left hand dashed line in FIG. 2c. After that time has elapsed, the gate is open or on and the gate is maintained on for 2 lifetimes of the fluorescent tag or approximately 200 nanoseconds for pyrenebutyrate. Thus, the total time in which the gating circuit 39 of FIG. 1 is kept on is indicated in FIG. 2c as the time between the two dashed lines, or from 50 to 200 nanoseconds after time zero. The process is then repeated.

In summary, the improved method of the present invention is carried out by tagging target materials with a fluorescent tag having a relatively long decay lifetime compared with competing ambient substances. Two exemplary tagging materials are rare earth-organo complexes of the type which have very long decay lifetimes, nearly $10^{-3}$ seconds, and pyrenebuterate, which has a lifetime in excess of 100 nanoseconds.

By keeping a fluorescence detection system gated off during most of the decay of ambient fluorescence, and then gating the detection system on to observe fluorescence of the tagging material, advantage is taken of the relatively long fluorescent lifetime of the tagging material. Further signal enhancement is obtained when the tagging material has very sharp emission spectra, as do rare earth complexes, by utilizing an interference filter to discriminate against unwanted wavelengths which fall outside the sharp emission passband of the interference filter.

While certain exemplary tagging materials have been described herein, other tagging materials may be known to those skilled in the art and the examples given herein are not intended to be restrictive. The method disclosed herein contemplates use of a fluorescent tag which has a long decay lifetime compared to the fluorescent decay lifetime of ambient substances. However, some preference has been given in the preferred embodiment to those fluorescent tags which also have sharp emission spectra which assist in discriminating against unwanted fluorescence.

I claim:

1. A method for fluorescent spectroscopy of a target substance comprising:
    isolating a target substance,
    tagging said target substance with a fluorescent tag having a long fluorescent decay lifetime compared to the longest of the decay lifetimes of competing untagged ambient substances,
    removing excess fluorescent tag,
    exciting the tagged target substance with at least one pulse of radiation, said pulse having a pulse duration which is short compared to the fluorescent decay lifetime of said fluorescent tag,
    detecting the fluorescence of said excited tagged target substances after the fluorescence of said ambient substances has substantially decayed.

2. The method of claim 1 whereby isolating said target substance is by means of chromatography.

3. The method of claim 1 whereby isolating said target substance is by means of combination with antibodies fixed on a substrate.

4. The method of claim 1 wherein said fluorescent tag is a fluorescent antibody specific to the target substance.

5. The method of claim 4 wherein said fluorescent antibody is an antibody conjugated with pyrenebutyrate.

6. The method of claim 1 wherein said fluorescent tag is a fluorescent rare earth-organo complex.

7. The method of claim 6 wherein said fluorescent rare earth-organo complex is europium benzoyltrifluoroacetonate.

8. The method of claim 1 wherein said fluorescent tag is pyrenebutyrate.

9. The method of claim 1 wherein said fluorescent detection system is gated on after five lifetimes of background fluorescence from the target.

10. The method of claim 1 wherein said exciting pulse is derived from a laser source.

11. The method of claim 10 wherein said exciting pulse is derived from a nitrogen laser source.

12. The method of claim 1 wherein said exciting pulse is derived from a pulsed dye laser excited by a nitrogen laser.

13. In a method of fluorescent spectroscopy for a target substance wherein at least one pulse of excitation radiation of relatively short duration is directed toward the target substance the improvement comprising, combining with said target substance a fluorescent tag specific to the target substance with fluorescent decay lifetime long compared with the longest of the fluorescent decay lifetimes of competing untagged ambient substances and detecting said tagged target substance after fluorescence of competing ambient substances substantially decayed.

14. The method of claim 13 wherein said fluorescent tag is a fluorescent rare earth-organo complex.

15. The method of claim 13 wherein said fluorescent tag is a fluorescent antibody specific to said target substance.

16. The method of claim 15 wherein the fluorescent antibody is an antibody conjugated with pyrenebutyrate.

17. A method for fluorescent spectroscopy of a target substance amid ambient substances comprising;
    tagging a target substance with a fluorescent tag specific to the target substance having a long fluorescent decay lifetime compared to the longest of the decay lifetimes of competing untagged ambient substances,
    removing excess fluorescent tag,
    exciting the tagged target substance for fluorescence with at least one pulse of radiation, said pulse having a pulse duration which is short compared to the fluorescent decay lifetime of said fluorescent tag,
    detecting the fluorescence of said excited tagged target substances after the fluorescence of said ambient substances has substantially decayed.

18. The method of claim 17 wherein said fluorescent tag is a fluorescent antibody specific to the target substance.

19. A fluorometer system for fluorescent spectroscopy of target substances comprising,
    an amount of target substance amid untagged ambient substances, said target substance tagged with a fluorescent tag having a long fluorescent decay lifetime compared to the longest of the decay lifetimes of competing ambient substances,
    radiation means having an output directed at said target substance for exciting said tagged target substance into fluorescence with at least one pulse of radiation, said pulse having a pulse duration which is short compared to the long fluorescent decay lifetime of said fluorescent tag, a fluorescence detector, disposed for receiving fluorescence from said tagged target substance, having means for detecting said fluorescence after the fluorescence of competing ambient substances has substantially decayed and having gating means connected to said detecting means for gating on said fluorescence detector after said fluorescence of competing ambient substances has substantially decayed, and means for correlating the detected fluorescence of the tagged target substance with the amount of tagged target substance 20. The apparatus of claim 19 wherein said target is supported on a solid matrix.

21. The apparatus of claim 19 wherein said radiation means is a pulsed dye laser.

22. The apparatus of claim 19 wherein said radiation means is a pulsed nitrogen laser.

23. The apparatus of claim 19 wherein said radiation means is a pulsed dye laser excited by a nitrogen laser.

24. The apparatus of claim 19 wherein said radiation means is a pulsed gas discharge.

25. The apparatus of claim 19 wherein said gating means is connected to a delay circuit means for establishing a selected time for fluorescent radiation from said ambient substances to substantially decay.

* * * * *